United States Patent
Nagahama et al.

(10) Patent No.: US 9,206,250 B2
(45) Date of Patent: Dec. 8, 2015

(54) MONOCLONAL ANTIBODIES AND METHOD OF IMMUNOLOGICAL ANALYSIS OF D-DIMER

(75) Inventors: Yutaka Nagahama, Tokyo (JP); Junko Nozaki, Tokyo (JP); George Sakurai, Tokyo (JP)

(73) Assignee: LSI MEDIENCE CORPORATION, Tokyo (JP)

( * ) Notice: Subject to any disclaimer, the term of this patent is extended or adjusted under 35 U.S.C. 154(b) by 0 days.

(21) Appl. No.: 13/637,973

(22) PCT Filed: Mar. 31, 2011

(86) PCT No.: PCT/JP2011/058286
§ 371 (c)(1),
(2), (4) Date: Sep. 27, 2012

(87) PCT Pub. No.: WO2011/125875
PCT Pub. Date: Oct. 13, 2011

(65) Prior Publication Data
US 2013/0011869 A1    Jan. 10, 2013

(30) Foreign Application Priority Data

Apr. 1, 2010 (JP) .................................. 2010-084863

(51) Int. Cl.
C07K 16/18 (2006.01)

(52) U.S. Cl.
CPC ............. *C07K 16/18* (2013.01); *C07K 2317/30* (2013.01); *C07K 2317/32* (2013.01); *C07K 2317/33* (2013.01); *G01N 2333/75* (2013.01)

(58) Field of Classification Search
None
See application file for complete search history.

(56) References Cited

U.S. PATENT DOCUMENTS

| 6,132,719 A | 10/2000 | Kohno et al. | |
| 2003/0108938 A1* | 6/2003 | Pickar et al. | 435/6 |
| 2009/0068682 A1* | 3/2009 | Matsuya | 435/7.9 |

FOREIGN PATENT DOCUMENTS

| EP | 0 122 478 A2 | 10/1984 |
| JP | 63-79900 A | 4/1988 |
| JP | 2001-21557 A | 1/2001 |
| JP | 2006-105633 A | 4/2006 |
| JP | 2006-234676 A | 9/2006 |
| WO | 2007/013709 A1 | 2/2007 |
| WO | WO 2009035510 A1 * | 3/2009 |

OTHER PUBLICATIONS

Haverkate et al., Anticlotting properties of fragments D from human fibrinogen and fibrin, European Journal of Clinical Investigation (1979), 9, 253-255.*
Olexa et al., Primary Soluble Plasmic Degradation Product of Human Cross-linked Fibrin. Isolation and Stoichiometry of the (DD)E Complex, Biochemistry 18(6), 1979, 991-995.*
Yokoyama et al., Production of Monoclonal Antibodies, In Current Protocols in Immunology, Supplement 71, (2006) 2.5.1-2.5.25.*
Charles W. Francis, et al.; Plasmic Degradation of Crosslinked Fibrin; J. Clin. Invest. (1980) 66(5) 1033-1043.
Akimi Takada, et al.; Study of Causes of False High Values in Plasma FDP and D-dimer Measurement; JJCLA (2005) 30(5) 721-726.
Katsuyuki Fukutake; Current situation of D-dimer test and the strategy for standarization; Seibutsu Shiryo Bunseki; (2009) vol. 32, No. 5, 380-385.
International Search Report for PCT/JP2011/058286 dated Jun. 10, 2011.
Doh et al., "Novel monoclonal antibody that recognizes new neoantigenic determinant of D-dimer," Thrombosis Research. 2006, vol. 118, pp. 353-360.
EP application No. 11765775.9, European Search Report, Apr. 17, 2014, 6 pages.
Rinsho Byouri; Medical Online; 1985, vol. 33, No. 12, pp. 1435-1439.

* cited by examiner

*Primary Examiner* — Galina Yakovleva
*Assistant Examiner* — Andrea S Grossman
(74) *Attorney, Agent, or Firm* — Kilpatrick Townsend & Stockton LLP (57) ABSTRACT

Provided are an antibody capable of specifically and accurately measuring digested products of stabilized fibrin (D-dimer), and a method and a reagent for measuring D-dimer using the antibody. The antibody specifically reacts with D-dimer, which is plasmin-digested products of stabilized fibrin, but does not react with fibrinogen or plasmin-digested products of fibrinogen, which include fragment X, fragment Y, fragment D1, and fragment E3, and does not react with dissociation products of DD/E monomer, which include fragment DD, fragment E1, and fragment E2.

5 Claims, 4 Drawing Sheets

MONOCLONAL ANTIBODIES AND METHOD OF IMMUNOLOGICAL ANALYSIS OF D-DIMER

CROSS-REFERENCES TO RELATED APPLICATIONS

The present application is a National Stage application under 35 U.S.C. §371, claiming priority to PCT/JP2011/058286, filed Mar. 31, 2011, which application claims the benefit of priority to Japanese Patent Application No. 2010-084863, filed Apr. 1, 2010, the teachings of which are incorporated herein by reference in their entirety for all purposes.

TECHNICAL FIELD

The present invention relates to novel monoclonal antibodies for accurately measuring D-dimer, plasmin digested products (D-dimer) of stabilized fibrin (in particular, human stabilized fibrin), and an immunologically analyzing method using the same antibodies.

The term "analysis" as used herein includes detection to judge the presence or absence of a substance, and measurement to quantitatively or semi-quantitatively determine the amount or activity of a substance.

BACKGROUND ART

Figure 1:
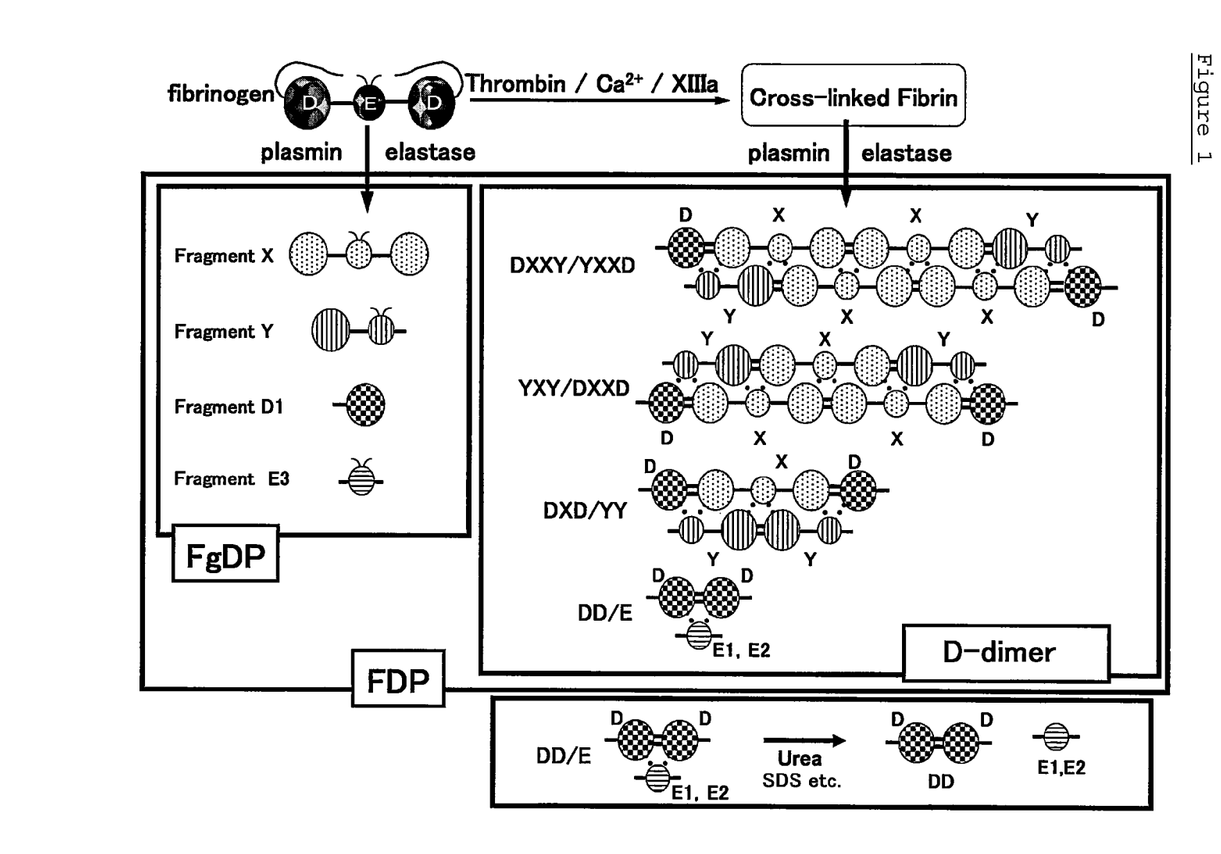
FIG. 1 schematically shows the structures of fibrinogen degradation products (FgDP) and stabilized fibrin degradation products (D-dimer).

Digested products of stabilized fibrin with various proteases are useful as a diagnostic marker in clinical diagnosis. For example, as shown in FIG. 1, plasmin-digested products of stabilized fibrin (cross-linked fibrin), i.e., DD/E monomer as a basic unit, and its polymers (DD/E polymers such as DXD/YY, YXY/DXXD, and DXXY/YXXD) are widely used as a diagnostic marker for disseminated intravascular coagulation (DIC). The plasmin-digested products of stabilized fibrin may be collectively referred to as, for example, D-dimer, D-D dimer, DD/E complex, or cross-linked fibrin degradation products (XDP).

The various proteases can also digest fibrinogen which is present in blood. For example, digested products of fibrinogen such as fragment X, fragment Y, fragment D1, and fragment E3, which contain one or more D domains and E domains in each of their molecules which are the components of D-dimer, may be generated by plasmin. The plasmin-digested products of fibrinogen may be collectively referred to as FgDP.

D-dimer generated by digesting stabilized fibrin with proteases, and digested products of fibrinogen (FgDP) generated by digesting fibrinogen with proteases may often coexist in the blood of a patient with thrombosis. Both digested products are referred to as FDP (see FIG. 1).

Although it was considered that the main component of D-dimer in the plasma of a patient with thrombosis was a DD/E fraction having a molecular weight of about 230 kDa, recently it has known that multimers having higher molecular weights, such as a DXD/YY fraction, a YXY/DXXD fraction, and a DXXY/YXXD fraction, are actually the main components (see non-patent literature 1).

In recent years, underlying diseases which result in death by thrombosis and/or embolism have shown an increasing trend, and a clinical laboratory test for detection of thrombus has been in progress. At an early stage, a measurement of FDP by determining digested products of fibrin/fibrinogen in serum using a polyclonal antibody against fibrinogen (Fbg) has been used for diagnosis of thrombosis. However, this method had a problem that it sometimes showed a falsely high level, due to an insufficient removal of fibrinogen.

In order to solve this problem, a D-dimer reagent which does not react with fibrinogen and can measure only digested products of stabilized fibrin (D-dimer) as DD/E complex in parallel with the measurement of FDP was required.

As a method for measuring D-dimer, for example, a method based on antigen-antibody reaction (i.e., a latex agglutination method or an ELISA method) in which a monoclonal antibody which recognizes D-dimer is immobilized on a solid phase such as latex particles or a plastic plate and D-dimer is bound to the immobilized monoclonal antibody is known (patent literature 1).

However, in this method based on antigen-antibody reaction, a currently-used monoclonal antibody immobilized on the solid phase does not only reacts with D-dimer, but also sometimes reacts with fragment X, fragment Y, fragment D1, and/or fragment E3 which have structures similar to that of D-dimer. When such monoclonal antibodies are used the monoclonal antibody immobilized to the solid phase may be bound to fragments other than D-dimer at the time of measurement, and thus, an inaccurate value is sometimes obtained.

To solve these problems, the following methods are disclosed. In this regard, it could not be said that monoclonal antibodies used in the following reagents were specific for D-dimer. For example, patent literature 2 has reported a D-dimer measuring reagent which reacts with multimers of DD/E fraction and the monomer of DD/E fraction, but does not react with X fraction, Y fraction, D fraction, and E fraction, and has at least 10% of reactivity to DD/E fraction, with respect to the reactivity to the tetramer of DD/E fraction. However, it has been revealed in patent literature 3 that antibody DD-M1653 (deposit No. FERM P-19687) concretely described in patent literature 2 reacts with multimers of DD/E fraction and the monomer of DD/E fraction, and X fraction and Y fraction, but does not react with D fraction and E fraction, and therefore, it cannot be said that this antibody is specific to D-dimer.

Further, patent literature 2 does not show whether or not D-dimer contained in a sample can be specifically and accurately measured. Patent literature 3 discloses that even if a monoclonal antibody having a relatively low specificity to D-dimer is used, the actual amount of D-dimer can be accurately measured using a D-dimer measuring kit consisting of a liquid reagent comprising a monoclonal antibody having a reactivity to D-dimer, and a carrier (or a solution containing the carrier) on which monoclonal antibody having a reactivity to D-dimer is immobilized, but D-dimer contained in a sample cannot be measured easily, specifically, and accurately.

Recently, due to advances in medicine, and advances in treatment and therapeutic drugs, for example, a thrombolytic agent is used to treat a patient with thrombosis. It is considered that fibrinolysis occurs in a fashion that it is unlikely to occur under the physiological environment, as described above, and the presence of digested products of fibrinogen including fragment D has become not to be ignored. Therefore, patent literature 4 discloses that when fragment D is present in a sample, in order to avoid to obtain a measured value lower than the actual value, due to inhibition of agglutination by interference of fragment D to a latex agglutination reaction, i.e., uncertain effects of fragment D derived from the sample, an excess amount of fragment D is previously and artificially added so that D-dimer can be accurately measured.

However, D-dimer in a sample cannot be specifically and accurately measured on use of only the intrinsic specificity of an antibody.

As described above, a D-dimer reagent specific to digested products of stabilized fibrin (D-dimer) has been desired, but an antibody capable of specifically and accurately measuring D-dimer using only the intrinsic specificity of a monoclonal antibody, or a reagent comprising such an antibody, has not been reported.

In addition, although the measurement of FDP and D-dimer using a plasma sample has become a commonly-used technique, there has been a problem that FDP and D-dimer rarely shows false high values. Non-patent literature 2 discloses that there is a possibility that FDP and D-dimer shows false high values, when coagulation and/or fibrinolysis are promoted by collecting plasma from a patient.

CITATION LIST

Patent Literature

[Patent literature 1] Japanese Unexamined Patent Publication (Kokai) No. 63-79900
[Patent literature 2] Japanese Unexamined Patent Publication (Kokai) No. 2006-105633
[Patent literature 3] Japanese Unexamined Patent Publication (Kokai) No. 2006-234676
[Patent literature 4] Japanese Unexamined Patent Publication (Kokai) No. 2001-21557

Non-Patent Literature

[Non-patent literature 1] Charles W. Francis, Victor J. Marder and Grant H. Barlow; Plasmic Degradation of Crosslinked Fibrin: CHARACTERIZATION OF NEW MACROMOLECULAR SOLUBLE COMPLEXES AND A MODEL OF THEIR STRUCTURE. J. Clin. Invest. (1980) 66(5): 1033~1043.
[Non-patent literature 2] Akimi Takada, Yoshiaki Maegawa, Yoshikazu Yamamoto, and Syuji Matuso; Study of Causes of False High Values in Plasma FDP and D-dimer Measurement. JJCLA. (2005) 30(5): 721~726.

SUMMARY OF INVENTION

Technical Problem

The present invention has been made to solve the above problems, and an object of the present invention is to provide a method and a reagent for specifically and accurately measuring digested products of stabilized fibrin (D-dimer) using at least one antibody which is not affected by fibrinogen and its digested products, i.e., fragment X, fragment Y, fragment D1, and fragment E3, and which does not react with fragment DD and fragments E1 and E2, which are generated by dissociating DD/E monomer.

Solution to Problem

Under these circumstances, the present inventors have conducted intensive studies, and have found that the use of at least one antibody which does not react with fibrinogen or its digested products, i.e., fragment X, fragment Y, fragment D1, and fragment E3, and does not react with fragment DD and fragments E1 and E2, which are generated by dissociating DD/E monomer, does not show a value lower than the actual value of D-dimer or a false high value due to the reaction with molecules other than D-dimer. The present invention is based on this finding to accomplish a method and a reagent for specifically and accurately measuring digested products of stabilized fibrin (D-dimer).

The present invention relates to:

[1] an anti-D-dimer antibody characterized in that the antibody specifically reacts with D-dimer which is plasmin-digested products of stabilized fibrin, and does not react with fibrinogen or plasmin-digested products of fibrinogen, which include fragment X, fragment Y, fragment D1, and fragment E3, and does not react with dissociation products of DD/E monomer, which include fragment DD, fragment E1, and fragment E2,

[2] a fragment of the antibody of [1],

[3] a hybridoma which produces the antibody of [1],

[4] a method of immunologically measuring D-dimer contained in a biological sample, using the antibody of [1] or the antibody fragment of [2], and

[5] a reagent for immunologically measuring D-dimer, comprising the antibody of [1] or the antibody fragment of [2].

Advantageous Effects of Invention

According to the antibody of the present invention, digested products of stabilized fibrin (D-dimer) can be specifically and accurately measured, even if a specimen suspected of containing a large amount of digested products of fibrinogen (FgDP) due to hyperfibrinolysis is analyzed. According to the latex reagent prepared using the antibody of the present invention, the inhibition of latex reaction by DD/E monomer can be avoided, and digested products of stabilized fibrin (D-dimer) can be measured more accurately.

Since only D-dimer generated by hyperfibrinolysis caused by a disease can be specifically measured using the antibody of the present invention, the effects of molecules which may be generated by artifact (for example, DD derived from dissociated DD/E monomer, modified D-dimer as described in Example 7 below, or the like) can be avoided.

DESCRIPTION OF EMBODIMENTS

The method of the present invention for specifically measuring D-dimer (including DD/E monomer and DD/E polymers) may be carried out using an antibody which does not react with at least fibrinogen or its plasmin-digested products, i.e., fragment X, fragment Y, fragment D1, and fragment E3, and dissociation products of DD/E monomer, i.e., fragment DD and fragments E1 and E2, and which specifically reacts to only D-dimer.

(1) Antibody

The antibody of the present invention may be obtained by a conventional method. The antibody may be a monoclonal antibody (MoAb) or a polyclonal antibody (PoAb), so long as it has the above-mentioned reactivities, and a monoclonal antibody is preferable. The origin of the antibody is not limited to a mouse, but a rat, a hamster, a rabbit, a goat, and a horse may be exemplified, and a mouse is preferable. The antibody is not limited to IgG, but may be IgM, IgA, IgE, IgD, or the like.

The antibody of the present invention may be prepared, for example, by cultivating a hybridoma capable of producing a desired MoAb in a medium or the abdominal cavity of a mammal. Such a hybridoma may be generally obtained by cell fusion of mouse myeloma with spleen cells from a mouse immunized with D-dimer in accordance with the basic method of cell fusion of Kohler and Milstein [see nature, 256, 495 (1975)].

The medium for cultivating a hybridoma may be any suitable medium for the cultivation of hybridoma, and an ERDF medium (Kyokuto Pharmaceutical Industrial Co., Ltd) containing bovine serum (Gibco), D-glucose (Wako Pure Chemical Industries, Ltd.), sodium hydrogen carbonate (Wako Pure Chemical Industries, Ltd.), and additives for medium RD-1 (Kyokuto Pharmaceutical Industrial Co., Ltd) is preferably used.

When the hybridoma is cultivated in a medium, it may be cultivated under the conditions of 37° C. and a 5% $CO_2$ concentration for about 3 days. When it is cultivated in the abdominal cavity of a mouse, it may be cultivated for about 14 days.

From the resulting culture or ascites fluid of a mammal, the monoclonal antibody may be separated and purified in accordance with a commonly used method for isolating and purifying proteins. Examples of the method include salting out with ammonium sulfate, ion-exchange column chromatography using ion exchange cellulose, molecular sieve column chromatography using a molecular sieve gel, affinity column chromatography using protein A binding polysaccharide, dialysis, and lyophilization.

The antibody fragment of the present invention, i.e., an antibody which is a fragment of MoAb of the present invention and contains an antigen-binding site which specifically reacts with D-dimer, may be, for example, Fab, Fab', F(ab')$_2$, or Fv. These fragments may be obtained, for example, by digesting the monoclonal antibody of the present invention with a protease, followed by a conventional method for the separation and purification of proteins.

As an antigen for preparing the antibody of the present invention, for example, DD/E monomer or DD/E polymers may be used. Examples of the DD/E polymers include dimer, trimer, tetramer, and pentamer. Hexamer or multimers having a higher molecular weight have a poor solubility in water. The antigen may be prepared from fibrinogen in accordance with a known method. The antigen may be purified from human or the like, or may be obtained by genetic engineering techniques. A commercially available antigen may be used.

The antibody of the present invention may be obtained by confirming that a prepared antibody does not react with at least fibrinogen or its plasmin-digested products, i.e., fragment X, fragment Y, fragment D1, and fragment E3, and does not react with dissociation products of DD/E monomer, i.e., fragment DD and fragments E1 and E2, and reacts with only D-dimer. This confirmation may be carried out by a known immunological measuring method, as shown in the Examples.

Since D-dimer includes DD/E monomer and DD/E polymers, and thus, have different molecular sizes and structures, it is considered that the reactivity of the antibody can be affected by steric hindrance or the like. Whether or not the measured value is affected by the content ratio of various molecules of D-dimer may be confirmed by adding various amounts of DD/E monomer to a constant amount of DD/E polymers, for example, as shown in the Examples.

(2) Measuring Method and Reagent

The measuring method and the reagent of the present invention may be carried out or prepared using the antibody which does not react with at least fibrinogen or its plasmin-digested products, i.e., fragment X, fragment Y, fragment D1, and fragment E3, and does not react with dissociation products of DD/E monomer, i.e., fragment DD and fragments E1 and E2, and reacts with only D-dimer.

The antibody of the present invention may be used alone to specifically and accurately measure D-dimer, and a plurality of antibodies, such as antibodies having different recognition sites, may be used in an appropriate combination.

The measuring method of the present invention may be carried out by a known immunological measuring method, except that the antibody of the present invention is used. More particularly, examples of the method include turbidimetric immunoassay (TIA), enzyme immunoassay (EIA), radioimmunoassay (RIA), latex agglutination method, fluorescence immunoassay, and immunochromatography. The antibody of the present invention may be utilized in these immunological measuring methods using the antibody of the present invention and other anti-D-dimer antibodies in a combination with two or more antibodies. In addition, since D-dimer can be specifically measured using the antibody of the present invention alone, the antibody of the present invention may be used in a combination with two or more antibodies, or the antibody of the present invention may be preferably utilized in the immunological measuring method using only one type of antibody of the present invention.

Hereinafter, the latex agglutination method using an insoluble carrier will be explained more specifically.

In the latex agglutination method, when an antibody which nonspecifically reacts is contained, nonspecific agglutination tends to occur in accordance with the principle of the method, and accurate measurement cannot be performed, and thus, it is preferable to use only the antibody of the present invention. Examples of the insoluble carrier include organic polymer particles, inorganic material particles, and red blood cells. Examples of the organic polymer particles include insoluble agarose, insoluble dextran, cellulose, and latex particles. Latex particles are preferable, and particles of polystyrene, styrene-methacrylic acid copolymer, styrene-glycidyl (meth) acrylate copolymer, styrene-styrene sulfonate copolymer, methacrylic acid polymer, acrylic acid polymer, acrylonitrile-butadiene-styrene copolymer, vinyl chloride-acrylic acid ester copolymer, poly(vinyl acetate-acrylate), or the like may be used. Examples of the inorganic material particles include silica and alumina. The average particle size of the particle may be appropriately selected according to a measuring apparatus or the like, and may be 0.05 to 0.50 µm.

Examples of a method for carrying an antibody on the insoluble carrier include a physical adsorption method and a chemical binding method, and the physical adsorption method is preferable in terms of ease of carrying operation.

A buffer, a sensitizer, a surfactant, and/or an inorganic salt may be appropriately added. A buffer showing a buffer action at pH 5-10, particularly pH 6-9, is preferable. Examples of the buffer include a phosphate buffer, a Tris buffer, an imidazole buffer, a triethanolamine-HCl buffer, and Good buffers. Examples of the Good buffers include a MES buffer, a Bis-Tris buffer, an ADA buffer, a PIPES buffer, a Bis-Tris-Propane buffer, an ACES buffer, a MOPS buffer, a BES buffer, a TES buffer, a HEPES buffer, a HEPPS buffer, a Tricine buffer, a Bicine buffer, and a TAPS buffer.

A sensitizer may be added in order to promote the agglutination rate or the like. The sensitizer is not limited, and polyvinylpyrrolidone, polyanion, polyethylene glycol, polysaccharides, or the like may be used.

Examples of the surfactant include a non-ionic surfactant, an anionic surfactant, a cationic surfactant, and an amphoteric surfactant.

An inorganic salt may be added in order to suppress the effects of salt concentration in a sample, or the like. Examples of the inorganic salt include sodium chloride and calcium chloride.

The measuring reagent for measuring the concentration of D-dimer in a sample may be in a form of two-component reagent consisting of a first reagent and a second reagent, or in a form consisting of one reagent. The two-component reagent consisting of the first reagent and the second reagent is preferable from the viewpoint of measurement accuracy, and examples are shown below.

The first reagent is composed of a buffer, and the second reagent is composed of antibody-sensitized latex particles, and a sensitizer, a surfactant, and/or an inorganic salt may be appropriately added. A preferable embodiment may be a reagent in which the first reagent is composed of a buffer, a sensitizer, and an inorganic salt, and the second reagent is composed of antibody-sensitized latex particles.

When the measurement is carried out using the measuring reagent, a method in which the first reagent is mixed with a sample in a reaction cell, the second reagent is further added thereto, and the degree of agglutination of the antibody-sensitized latex particles is optically measured; a method in which the first reagent and the second reagent are mixed in a reaction cell, a sample is further added thereto, and the degree of agglutination of the antibody-sensitized latex particles is optically measured; or the like may be used.

A sample which may be analyzed by the present invention may be, for example, liquid biological samples, such as blood, plasma, serum, or urine.

For example, agglutination reaction is carried out using the exemplified reagent, and the degree of agglutination is optically observed, with respect to D-dimer solutions of known concentrations and a sample, and compared with each other to determine the concentration of D-dimer in the sample. More particularly, D-dimer solutions of known concentrations are measured at two or more different concentrations (it is preferable that a solution having a D-dimer concentration of 0 µg/mL is contained.), and a standard curve is prepared based on the relationship between the amount of change in optical density and the D-dimer concentrations. Next, the sample is measured, and the concentration is determined from the amount of change in optical density, using the standard curve, and the value is regarded as the concentration of D-dimer. In the method of optically detecting the degree of agglutination of the antibody-sensitized latex particles, the measurement is carried out using an optical apparatus for measuring scattered light intensity, absorbance, or transmitted light intensity. An appropriate wavelength for measurement may be selected from 300 to 2400 nm, preferably 300 to 1000 nm, and more preferably 300 to 800 nm. With respect to a measuring method, the particle size or the concentration of the antibody-sensitized latex particles used, and the reaction time are selected, and an increase or a decrease in scattered light intensity, absorbance, or transmitted light intensity is measured. These methods may be used in a combination thereof.

As the conditions of the immunological reaction, known conditions may be selected, and the temperature in the reaction is preferably 10 to 50° C., and particularly 20 to 40° C. The reaction time may be appropriately selected.

EXAMPLES

The present invention now will be further illustrated by, but is by no means limited to, the following Examples.

Example 1

Preparation of Antigens and Various Molecules (1) Preparation of D-dimer

D-dimer was prepared basically in accordance with the method of Stephanie A. Olexa and Andrei Z. Budzynski (1978); Circulation, Suppl. 58, 119, the method of Olexa et al. (1979); and Biochim. Biophys. Acta 576, 39-50. Bovine thrombin (Mochida Pharmaceutical Co., Ltd.) and calcium chloride were added to human fibrinogen (Enzyme Research Laboratories). The mixture was reacted at 37° C. for 2 hours to convert fibrinogen into fibrin, and centrifuged to separate fibrin from non-coagulable substances. The fibrin was suspended in a Tris-HCl buffer (pH 7.8) containing calcium chloride. Human plasmin (Chromogenix) was added to the suspension under the conditions of 37° C. Aprotinin (Pentapharm.) was added to stop the digestion reaction, and the reaction product was passed through a lysine-Sepharose column to remove the plasmin. The eluate was a mixture of D-dimer having different molecular weights.

The eluate was applied to a Sephacryl S-300 column equilibrated with a Tris-HCl buffer (pH 7.5) containing calcium chloride (solution A), and fractionated by molecular sieve chromatography using solution A as a developing solution. The resulting fractions were subjected to electrophoresis (SDS-PAGE) and Western blotting to identify and isolate D-dimer fractions. The obtained D-dimer fractions were used as immunogens, and antigens for enzyme immunoassay (ELISA) or latex (LTX) to select hybridomas which produced an anti-D-dimer monoclonal antibody.

(2) Preparation of Fragment DD, Fragment E1, and Fragment E2

A fraction of D-dimer having the lowest molecular weight (DD/E monomer) obtained above was incubated in a 3 mol/L urea-50 mmol/L citrate solution (pH 5.5) at 37° C. for 4 hours. The reaction product was applied to a Sepharose CL-6B column equilibrated with a 50 mmol/L Tris-HCl buffer (pH 7.4)-28 mmol/L sodium citrate-0.1 mol/L sodium chloride solution, and developed using the same solution. The fractionated fragment DD, fragment E1, and fragment E2 were identified and isolated by electrophoresis (SDS-PAGE) and Western blotting.

(3) Preparation of Plasmin-Digested Products of Human Fibrinogen

After calcium chloride was added to human fibrinogen (Enzyme Research Laboratories), human plasmin (Chromogenix) was further added, and a reaction was carried out at 37° C. for 2 hours. Aprotinin (Pentapharm.) was added to stop the reaction. The reaction product was applied to a Sephacryl S-300 column equilibrated with a Tris-HCl buffer (pH 7.5), and fractionated to fragment X, fragment Y, fragment D1, and fragment E3 by gel filtration. These fragments were used as antigens for ELISA or LTX to select hybridomas which produced an anti-D-dimer monoclonal antibody.

Example 2

Preparation of Monoclonal Antibodies (1) Preparation of Immunized Spleen Cells

The DD/E monomer solution prepared in Example 1 was mixed with an equal amount of Freund's complete adjuvant until emulsified (an immunogen mixture), and a mouse was immunized with the immunogen mixture by intracutaneous administration (first immunization). After 2 weeks, the mouse was immunized in a similar fashion, with the immunogen mixture by intracutaneous administration (second immunization). The mouse was immunized with the immunogen mixture by intracutaneous administration every two weeks, totally 4 times. After 2 weeks from the fourth immunization, the DD/E monomer solution prepared in Example 1 was mixed with an equal amount of aluminum hydroxide gel, and the mixture was administered into the spleen of the mouse (final immunization). After 3 days from the final immunization, the spleen was removed from the mouse and used for cell fusion.

(2) Cell Fusion

Spleen cells were collected in an ERDF medium from the aseptically removed spleen. The spleen cells were transferred to a centrifuge tube and centrifuged. The resulting pellet was suspended in an ERDF medium, and the number of living spleen cells was counted.

Mouse myeloma cells P3U1 which had been cultivated were mixed with the spleen cells, and centrifuged. The resulting pellet was suspended in PEG1500, and subsequently suspended in an ERDF medium to fuse the cells. The pellet was suspended in an ERDF medium containing bovine serum, hypoxanthine, aminopterin, thymidine, and RD-1. The cell suspension was cultivated in a 96-well cell culture plate in a carbon dioxide gas incubator containing 5% carbon dioxide gas.

(3) Establishment of Hybridomas

After cultivation for about 13 days, each culture supernatant was collected to confirm the presence of the desired antibody using an ELISA method. An anti-mouse immunoglobulin antibody diluted with phosphate buffered saline (PBS) was dispensed to a 96-well ELISA plate, and the plate was allowed to stand at 4° C. overnight. The plate was washed with 0.05% Tween-20 containing phosphate buffered saline (T-PBS) 4 times. After the washing, each culture supernatant was dispensed, and the plate was allowed to stand at 4° C. overnight. The plate was washed with T-PBS 4 times, and the DD/E monomer fraction prepared in Example 1 and diluted with T-PBS was dispensed, and reacted at room temperature for 2 hours. The plate was washed with T-PBS 4 times, and peroxidase (HRP)-labeled anti-human fibrinogen polyclonal antibody diluted with T-PBS was dispensed, and reacted at room temperature for 1 hour. The plate was washed with T-PBS 4 times, and a TMB reagent (Kirkegaard & Perry Laboratories, Inc.) was dispensed, and reacted at room temperature for 10 minutes. A 1 mol/L phosphate solution was added to stop the reaction, and an absorbance at 450 nm was measured. Similarly, the reactivity against fibrinogen and fragment D1 was confirmed, and hybridomas which reacted with the DD/E monomer fraction but did not react with fibrinogen or fragment D1 were cloned by limiting dilution to establish the clones. The above cell fusion was repeated three times, and 18 clones were established from three immunized mice.

(4) Preparation of Monoclonal Antibodies

Each hybridoma obtained above was intraperitoneally administered to a BALB/c mouse to which pristane had been intraperitoneally administered. Ascites fluid was collected after about two weeks. The ascites fluid was centrifuged, and solid ammonium sulfate was gradually added to the supernatant. The mixture was stirred on ice for 30 minutes, and allowed to stand for 60 minutes, and centrifuged. The resulting precipitate was dissolved in a small volume of Tris-HCl buffer (pH 7.5) (solution B), and applied to a Q Sepharose column equilibrated with solution B. Each antibody was eluted with solution B containing 0.16 mol/L NaCl to obtain purified anti-D-dimer antibodies.

(5) Screening of Anti-D-Dimer Antibodies by ELISA

The reactivities of the purified antibodies obtained above against fibrinogen-related fragments were confirmed by ELISA to select hybridomas. Fibrinogen (Fbg), DD/E monomer (DD/E mono), DD/E polymers (DD/E poly), fragment X, fragment Y, fragment D1, and fragment E3 were used as antigens.

The results are shown in Table 1. The definitions of the symbols used in Table 1 are shown in Table 2. It was confirmed that 18 clones obtained did not react with fibrinogen or digested products of fibrinogen (fragments X, Y, D1, and E3).

TABLE 1

| Clones | Fbg | DD/E mono | DD/E poly | X | Y | D1 | E3 | Buffer |
|---|---|---|---|---|---|---|---|---|
| MF-1 | − | ++ | +++ | − | − | − | − | − |
| MF-2 | − | ++ | ++ | − | − | − | − | − |
| MF-3 | − | + | ++ | − | − | − | − | − |
| MF-4 | − | + | ++ | − | − | − | − | − |
| MF-5 | − | + | +++ | − | − | − | − | − |
| MF-6 | − | + | +++ | − | − | − | − | − |
| MF-7 | − | ++ | ++ | − | − | − | − | − |
| MF-8 | − | +++ | +++ | − | − | − | − | − |
| MF-9 | − | ++ | +++ | − | − | − | − | − |
| MF-10 | − | ++ | +++ | − | − | − | − | − |
| MF-11 | − | ++ | +++ | − | − | − | − | − |
| MF-12 | − | ++ | +++ | − | − | − | − | − |
| MF-13 | ± | +++ | +++ | − | − | − | − | − |
| MF-14 | − | +++ | +++ | − | − | − | − | − |
| MF-15 | − | +++ | +++ | − | − | − | − | − |
| MF-16 | − | +++ | +++ | − | − | − | − | − |
| MF-17 | ± | +++ | +++ | − | − | − | − | − |
| MF-18 | − | +++ | +++ | − | − | − | − | − |
| Blank | − | − | − | − | − | − | − | − |

TABLE 2

| Absorbance | |
|---|---|
| ~0.2 | − |
| ~0.5 | ± |
| ~1.0 | + |
| ~1.5 | ++ |
| 1.5~ | +++ |

Example 3

Preparation of Reagent for Measuring D-Dimer by Latex Agglutination and Evaluation of Anti-D-Dimer Antibodies (1) Preparation of Polystyrene Latex Particles Sensitized with Anti-D-Dimer Antibody Each antibody purified in Example 2 was dissolved in a Tris-HCl buffer (pH 8.0), and 5 mL of polystyrene latex particles suspension (JSR) was added to the antibody solution, and stirred at room temperature for 60 minutes. To this mixture, a Tris-HCl buffer (pH 8.0) containing bovine serum albumin (BSA) was added, and stirred at room temperature for 60 minutes, and centrifuged. The resulting precipitate was suspended in a Tris-HCl buffer (pH 8.0) to prepare each suspension of latex sensitized with an anti-D-dimer antibody.

(2) Screening of Anti-D-Dimer Antibodies by Latex Agglutination
Confirmation of the Effect of DD/E Monomer and Fragment D1 in Sample Against Anti-D-Dimer Antibodies Obtained in Example 2
(2-1) Preparation of Standard Solutions and Samples As standard solutions, the purified D-dimer was diluted with a Tris-HCl buffer (pH 8.0) containing BSA so that the concentration became 0, 2, 8, 32, 48, and 60 μg/mL.

On the other hand, as samples, after the purified D-dimer (DD/E polymers) was diluted with a Tris-HCl buffer (pH 8.0) containing BSA to a concentration of 10 μg/mL, the DD/E monomer was further added to the DD/E polymer solution so that the concentration of the DD/E monomer became 0 to 20 μg/mL (each 0, 4, 8, 12, 16, and 20 μg/mL) while the concentration of the DD/E polymers was constant. Further, as other samples, fragment D1 was added to the DD/E polymer solution so that the concentration of fragment D1 became 0 to 100 μg/mL (each 0, 20, 40, 60, 80, and 100 μg/mL) while the concentration of the DD/E polymers was constant.

(2-2) Measuring Method

To 5 μL of each standard solution, 160 μL of a Tris-HCl buffer (pH 8.0) containing BSA was added, and the mixture was allowed to stand at 37° C. for about 5 minutes. Further, 80 μL of the suspension of latex sensitized with an anti-D-dimer antibody was added and stirred, and a change within about 10 minutes in absorbance at 800 nm was measured to prepare a standard curve. Similarly, each sample prepared above was measured, and the measured value was determined based on the standard curve. Absorbance was measured using an automatic analyzer Hitachi 7170.

Figure 2:
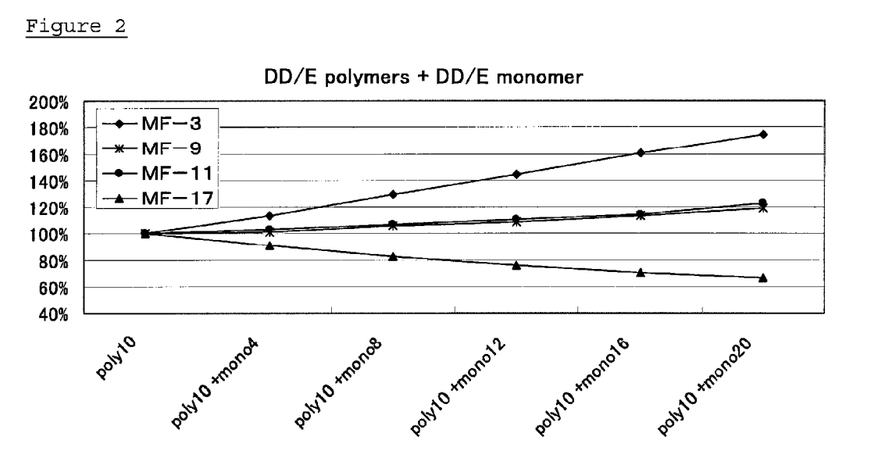
FIG. 2 shows the effects of DD/E monomer contained in samples on latex agglutination using various anti-D-dimer antibodies.
Figure 3:
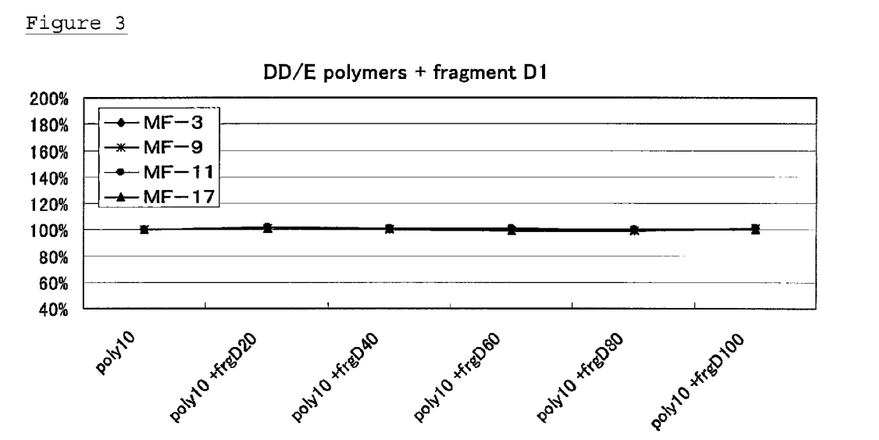
FIG. 3 shows the effects of fragment D1 contained in samples on latex agglutination using various anti-D-dimer antibodies.

Part of the results is shown below. As shown in FIG. 2, the latex agglutination reaction of antibody MF-17 was inhibited by the DD/E monomer, and when the other three antibodies (MF-3, MF-9, and MF-11) were used, the measured values increased dependently on the concentration of DD/E monomer added. As shown in FIG. 3, when the concentration of fragment D1 increased, no effects were observed in the latex agglutination reaction using any one of eighteen antibodies including the four antibodies above.

Antibodies other than MF-17 affected by the presence of DD/E monomer included MF-13, MF-14, MF-15, MF-16, and MF-18. These antibodies did not react with fragment X, fragment Y, fragment D1, and fragment E3, and did not affect the latex agglutination. Because the DD/E monomer is part of D-dimer, and the antibodies in which the latex agglutination reaction was inhibited by the increased DD/E monomer are not suitable to a latex agglutination assay, twelve antibodies except the six clones having the same reactivity as that of MF-17 were selected.

(3) Confirmation of Immunoglobulin Class and Specificity of Monoclonal Antibodies The selected twelve antibodies were subjected to an isotyping kit (Dainippon Pharmaceutical) to identify the immunoglobulin class. The results are shown in Table 3.

TABLE 3

| No. | Clones | Subclass |
|---|---|---|
| 1 | MF-1 | IgG1, κ |
| 2 | MF-2 | IgG1, κ |
| 3 | MF-3 | IgG1, κ |
| 4 | MF-4 | IgG1, κ |
| 5 | MF-5 | IgG1, κ |
| 6 | MF-6 | IgG1, κ |
| 7 | MF-7 | IgG1, κ |
| 8 | MF-8 | IgG2a, κ |
| 9 | MF-9 | IgG1, κ |
| 10 | MF-10 | IgG2a, κ |
| 11 | MF-11 | IgG1, κ |
| 12 | MF-12 | IgG1, κ |

Hereinafter, the results for MF-3 and MF-12 will be shown as typical clones.

Example 4

Identification of Recognition Site of Monoclonal Antibodies (1) Confirmation by Western Blotting Western blotting was carried out using NewPAGE/Western Bleeze (Invitrogen). The outline of the experimental procedure was as follows.

Fibrinogen (Fbg), D-dimer, and digested products of fibrinogen (FgDP) were subjected to SDS-polyacrylamide gel electrophoresis (SDS-PAGE) and Native-PAGE in the presence and the absence of dithiothreitol. The gels after PAGE were used to carry out Western blotting, i.e., immunostaining using an anti-Fbg antibody, antibody MF-13, and antibody MF-12. In contrast with the anti-Fbg antibody as a control, no bands were detected in any sample by monoclonal antibody MF-3 or MF-12.

(2) Confirmation by ELISA

Since it was considered from the results of electrophoresis that electrical load caused the dissociation of the E-D bond and the change in the structure of the site recognized by an antibody, an analysis was carried out by ELISA in a similar fashion to that of Example 2, to confirm whether or not the presence of the E-D bond affected the antibody reaction.

D-dimer is composed of DD/E as a constitutional unit, and the D domains covalently bind to each other, and the D domain electrically binds to the E domain by recognizing the three-dimensional structure. Therefore, fragment DD can be easily separated from fragment E1 and fragment E2 by urea, SDS, or the like. It is known that the separated fragment DD and fragments E1 and E2 can be reconstructed by the removal of urea, and return to the same structure of that of the original molecule. Since fragment E3, which is FgDP, has a similar structure to those of fragment E1 and fragment E2, but does not have a binding site to the D domain, the E-D bond cannot be formed. Since DD/E monomer is not dissociated in the environment of the living body, fragment E1 and fragment E2 derived from DD/E do not bind to fragment D1 which is FgDP.

The molecules described below were prepared as antigens for ELISA:
(1) DD/E monomer (part of D-dimer),
(2) Fragment DD (prepared by treating DD/E monomer with urea),
(3) Fragment D1 (part of FgDP),
(4) Fragment E1 and Fragment E2 (prepared by treating DD/E monomer with urea),
(5) Fragment E3 (part of FgDP),
(6) Fragment DD+Fragments E1 and E2 [prepared by reacting (2) with (4) in vitro for a predetermined period of time],
(7) Fragment DD+Fragment E3 [prepared by reacting (2) with (5) in vitro for a predetermined period of time],
(8) Fragment D1+Fragments E1 and E2 [prepared by reacting (3) with (4) in vitro for a predetermined period of time],
(9) Fragment D1+Fragment E3 [prepared by reacting (3) with (5) in vitro for a predetermined period of time]

Figure 4:
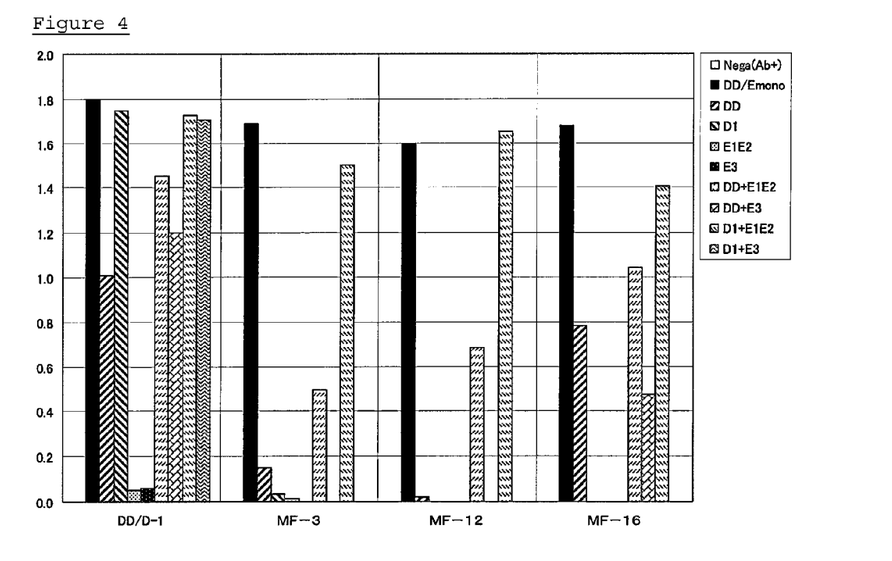
FIG. 4 shows the reactivities of various anti-D-dimer antibodies to DD/E or its constitutional fragments, fragment D1 or fragment E3 as digested products of fibrinogen (FgDP), or mixtures of these fragments by ELISA.

The results of ELISA are shown in FIG. 4. Antibody MF-3 and antibody MF-12 did not react with fragment DD (2), or fragment E1 and fragment E2 (4), which had been dissociated by treating DD/E monomer with urea, but reacted with a mixture of fragment DD and fragments E1 and E2 (6), or a mixture of fragment D1 and fragments E1 and E2 (8). However, antibody MF-3 and antibody MF-12 did not react with a mixture of fragment DD and fragment E3 (7), or a mixture of fragment D1 and fragment E3 (9). It was proved by these results that antibody MF-3 and antibody MF-12 reacted with a substance in which the D domain bound to the E domain.

Since the recognition site of antibody DD/D-1, which was used as a control, was located in the D domain, antibody DD/D-1 reacted with DD/E monomer (1), fragment DD obtained by urea treatment (2), or fragment D1 (3), but did not react with fragment E1 and fragment E2 (4), or fragment E3 (5). Antibody DD/D-1 also reacted with a mixture of fragment DD and fragments E1 and E2 (6), a mixture of fragment DD and fragment E3 (7), a mixture of fragment D1 and fragments E1 and E2 (8), or a mixture of fragment D1 and fragment E3 (9). Since fragment E3 did not form the E-D bond with fragment DD or fragment D1, but contained the D domain, the signal was detected in the ELISA.

When the reactivities of antibody MF-16, in which the latex reaction was inhibited by DD/E monomer, were confirmed by ELISA, antibody MF-16 reacted with fragment DD (2), but did not react with fragment E1 and fragment E2 (4). Since antibody MF-16 reacted with a mixture of fragment D1 and fragments E1 and E2 (8), it was considered that two molecules of fragment D1 bound to fragments E1 and E2, and the two D domains were close to each other, and the antibody reacted with the structure. The five antibodies (MF-13, MF-14, MF-15, MF-17, and MF-18) other than antibody MF-16, in which the latex reaction was inhibited by DD/E monomer, reacted with fragment DD (2). From the results, these five antibodies having a reactivity against fragment DD were not suitable to a D-dimer latex reagent using a single antibody, because the latex agglutination was inhibited by DD/E monomer.

As described above, it was proved that antibody MF-3 and antibody MF-12 did not react with fragments derived from FgDP, and specifically reacted with digested products of fibrin, and D-dimer having the E-D bond.

Further, it was considered from the results of Western blotting and ELISA that the recognition site of these antibodies was the D domain and/or the E domain of D-dimer having the E-D bond.

Example 5

Figure 5:
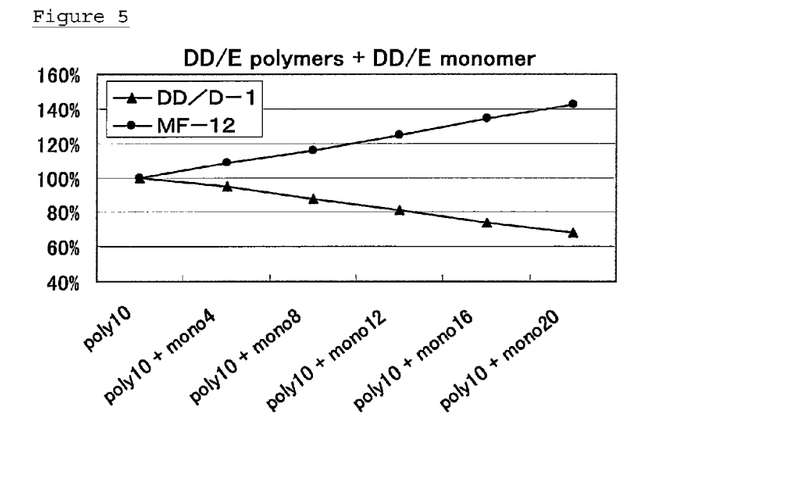
FIG. 5 shows the effects of DD/E monomer contained in samples on latex agglutination using various anti-D-dimer antibodies.
Figure 6:
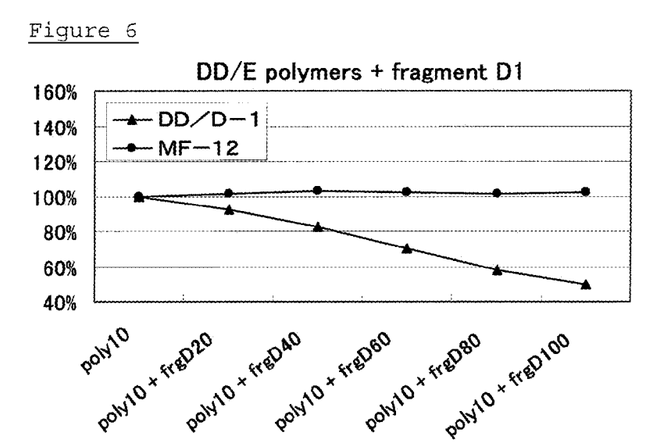
FIG. 6 shows the effects of fragment D1 contained in samples on latex agglutination using various anti-D-dimer antibodies.

Confirmation of Specificity and Accuracy of Latex Agglutination Reagents Using the Antibody of the Present Invention and Conventional Antibody The reactivity of antibody MF-12 and antibody DD/D-1 against DD/E monomer and fragment D1 in DD/E polymers was confirmed in a similar fashion to that of Example 3. As shown in FIGS. 5 and 6, when antibody MF-12 was used, the measured values increased dependently on the concentration of DD/E monomer added, and the latex agglutination reaction was not inhibited by fragment D1. By contrast, when antibody DD/D-1 was used, the latex agglutination reaction was inhibited dependently on the concentration of DD/E monomer or fragment D1 added.

Example 6

Confirmation of Specificity and Accuracy of Reagent for Measuring D-Dimer of the Present Invention A sample containing the purified D-dimer (DD/E polymers) and fragment D1 prepared in Example 3 was used to compare antibody MF-12 with the conventional D-dimer reagents (products A, B, and C). The measurement was carried out in accordance with the attached manuals, using an automatic analyzer Hitachi 7170. The measurement using antibody MF-12 was carried out by the latex agglutination described in Example 3.

Figure 7:
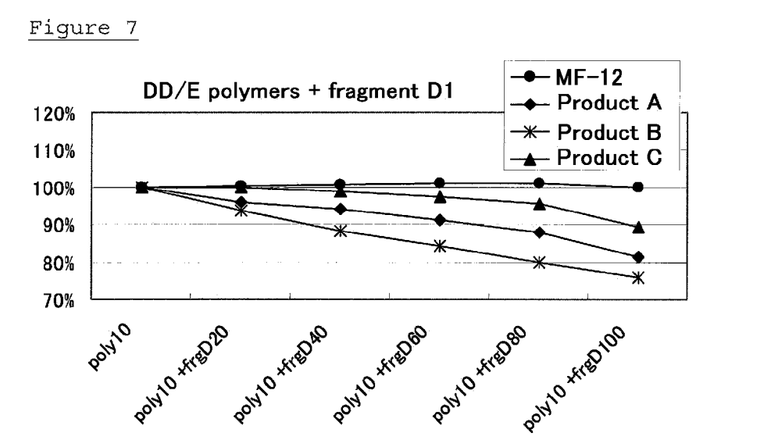
FIG. 7 shows the effects of fragment D1 contained in samples on latex reagents using the anti-D-dimer antibody of the present invention, and commercially available conventional D-dimer reagents.

The results are shown in FIG. 7. It was confirmed that when the three conventional D-dimer reagents were used, the measured values of D-dimer decreased dependently on an increase in the amount of fragment D1 contained in the sample, and when the reagent using antibody MF-12 was used, fragment D1 did not affect the measured value of D-dimer at a concentration of 100 µg/mL or less.

It was confirmed from the results that the reagent for measuring D-dimer using antibody MF-12 was not affected by fragment D1, which was digested product of fibrinogen, and D-dimer could be accurately measured, in comparison with the conventional D-dimer reagents.

Example 7

Confirmation and Inspection of Specificity of Reagent for Measuring D-Dimer of the Present Invention in Plasma Samples Citrate-added plasma samples were measured to confirm the difference in the specificity of the reagent for measuring D-dimer of the present invention and the conventional reagent for measuring D-dimer used in Example 6. Product A was used as the conventional reagent for measuring D-dimer. The measurement was carried out in a similar fashion to that of Example 6.

For the inspection, frozen samples which had been prepared as citrate-added plasma samples were thawed at 37° C. for 30 minutes, and used. Two typical results are selected from 12 specimens, and shown in Table 4. In specimen 1, the measured values of D-dimer did not change in the conventional reagent and the reagent (antibody MF-12) of the present invention, regardless of the number of freeze and thawing cycles. In specimen 2, the D-dimer value measured using the conventional reagent increased about three times due to freezing and thawing. In contrast, such a significant change was not observed when the D-dimer reagent of the present invention using antibody MF-12 was used (Table 4).

It was reported in non-patent literature 2 that fibrin clot was formed in plasma samples in rare cases. It was considered that the original D-dimer did not change by the freeze and thawing of the sample, but fibrin clot formed by artifact was modified to generate D-dimer, and as a result, the measured value by the conventional method increased.

TABLE 4

|  | Conventional reagent Freeze-thaw (once) | Conventional reagent Freeze-thaw (twice) | MF-12 Freeze-thaw (once) | MF-12 Freeze-thaw (twice) |
| --- | --- | --- | --- | --- |
| Specimen 1 | 27.52 | 26.89 | 15.23 | 16.76 |
| Specimen 2 | 45.89 | 145.70 | 21.96 | 26.43 |

Figure 8:
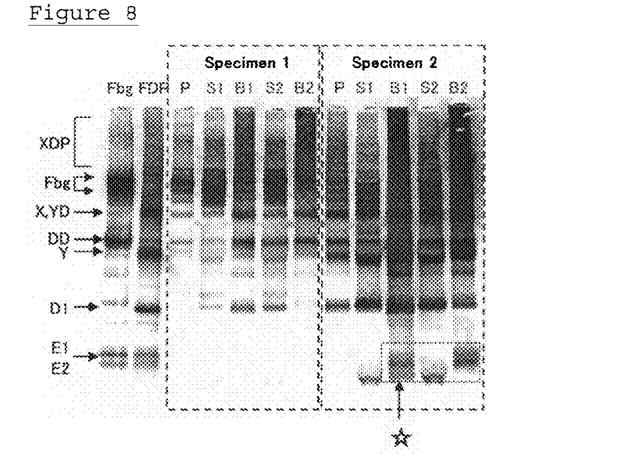
FIG. 8 shows the results of electrophoresis and Western blotting (detected with anti-Fbg antibody) of
(S) supernatants adsorpted samples by each antibody,
(B) substances bound to each antibody,
(P) untreated plasma as a control,
which were obtained by an adsorption treatment of frozen and thawed plasma samples with the antibody of the present invention (conventional antibody for comparison).

To investigate the cause of the variation in measured value due to freezing and thawing of specimen 2, the antibody of the present invention (antibody MF-12) and the conventional antibody (antibody DD/D-1) were used to carry out adsorption treatment of the specimen, and the resulting supernatants (S), substances which bound to each antibody (B), and untreated plasma (P) were analyzed by Western blotting. More particularly, fraction (S), fraction (B), and fraction (P) were electrophoresed by 3-8% SDS-PAGE under non-reducing conditions, transferred to a polyvinylidene fluoride (PVDF) membrane, and detected using an anti-Fbg antibody. The results are shown in FIG. 8. Lanes S1 and B1 indicate the results of antibody DD/D-1, and lanes S2 and B2 indicate the results of antibody MF-12. The arrows at the left indicate Fbg, plasmin-digested products of stabilized fibrin (XDP, YD, DD, and E1E2), and digested products of fibrinogen (X, Y, and D1).

In specimen 1, when the substance bound to antibody DD/D-1 (B1) was compared to that bound to antibody MF-12 (B2), there was no difference except that the band of fragment D1 was detected in B1. This is because antibody DD/D-1 recognizes the D domain. However, in specimen 2 in which the D-dimer value increased due to freezing and thawing, in addition to the band of fragment D1, a band having a molecular weight lower than that of fragment E2 was detected in only lane B1 (the star and arrow in the center). In contrast, this band was not detected by antibody MF-12. It was considered that this band was derived from fragment E, because it was not detected by Western blotting using an antibody which recognized the D domain.

It is considered that the presence of the E fraction having a molecular weight lower than that of fragment E2 is fragment E3 generated by the digestion of fibrinogen, but it is unlikely that fragment E3 is present alone in B1, because antibody DD/D-1 recognizes the D domain. Further, since fragment E3 does not have an ability to bind to the D domain, as described in Example 4, fragment E3 does not bind to the D domain and does not bind to antibody DD/D-1.

From these results, there was a high possibility that the increased D-dimer due to freezing and thawing was generated by artifact, and it was suggested that the D-dimer was a molecule in which DD/E was modified, the E-D bond was not normal, and the E fraction having a low molecular weight was contained.

As described above, it was shown that the D-dimer reagent of the present invention using antibody MF-12 was a reagent which was not affected by the D-dimer generated by artifact and which was capable of accurately measuring the D-dimer level in the living body.

INDUSTRIAL APPLICABILITY

The antibody of the present invention can be used in the measurement of plasmin-digested products of stabilized fibrin (D-dimer), which is useful as a diagnostic marker for disseminated intravascular coagulation (DIC).

Although the present invention has been described with reference to specific embodiments, various changes and modifications obvious to those skilled in the art are possible without departing from the scope of the appended claims.

The invention claimed is:

1. An anti-D-dimer antibody, which specifically reacts with a D-dimer, wherein the D-Dimer is a plasmin digested product of stabilized fibrin, but does not react with (1), (2) and (3) as follows:
    (1) Fibrinogen,
    (2) fragment X, fragment Y, fragment D1 and fragment E3, which are plasmin-digested products of fibrinogen; and
    (3) fragment DD, fragment E1 and fragment E2, which are dissociation products of a DD/E monomer, wherein said DD/E monomer is a basic unit of plasmin-digested products of stabilized fibrin.

2. A functional fragment of the antibody according to claim 1.

3. A hybridoma which produces the antibody according to claim 1.

4. A method of immunologically measuring the D-dimer contained in a biological sample, comprising the steps of:
    labeling the antibody of claim 1 or a functional fragment thereof with a detectable moiety,
    bringing the biological sample into contact with the labeled antibody or fragment to form an immunological complex, and
    detecting the detectable moiety from the immunological complex, and
    correlating it to a concentration; or
    immobilizing the antibody of claim 1 or a functional fragment thereof on a solid phase,
    bringing the biological sample into contact with the solid phase carrying the antibody or fragment,
    detecting the degree of agglutination, and
    correlating it to a concentration.

5. A reagent for immunologically measuring the D-dimer, comprising the antibody according to claim 1 or a functional fragment thereof.

* * * * *